US008083664B2

(12) United States Patent
Davis (10) Patent No.: US 8,083,664 B2
(45) Date of Patent: Dec. 27, 2011

(54) SURGICAL STABILIZERS AND METHODS FOR USE IN REDUCED-ACCESS SURGICAL SITES

(75) Inventor: John W. Davis, Sunnyvale, CA (US)

(73) Assignee: MAQUET Cardiovascular LLC, San Jose, CA (US)

( * ) Notice: Subject to any disclaimer, the term of this patent is extended or adjusted under 35 U.S.C. 154(b) by 1389 days.

(21) Appl. No.: 11/137,267

(22) Filed: May 25, 2005

(65) Prior Publication Data

US 2006/0270910 A1 Nov. 30, 2006

(51) Int. Cl.
*A61B 17/00* (2006.01)
(52) U.S. Cl. .......................................................... 600/37
(58) Field of Classification Search .................... 600/37, 600/114, 201, 204, 205, 210; 606/1
See application file for complete search history.

(56) References Cited

U.S. PATENT DOCUMENTS

| | | |
|---|---|---|
| 452,131 A | 5/1891 | Haughawout |
| 810,675 A | 1/1906 | Richter |
| 820,721 A | 5/1906 | Kohlbach |
| 1,706,500 A | 3/1929 | Smith |
| 2,082,782 A | 6/1937 | Allen |
| 2,233,561 A | 3/1941 | Kalle |
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,096,962 A | 7/1963 | Meijs |
| 3,361,133 A | 1/1968 | Kimberley et al. |
| 3,392,722 A | 7/1968 | Jorgensen |
| 3,466,079 A | 9/1969 | Mammel |
| 3,584,822 A | 6/1971 | Oram |
| 3,683,926 A | 8/1972 | Suzuki |
| 3,720,433 A | 3/1973 | Rosfelder |

(Continued)

FOREIGN PATENT DOCUMENTS

DE 31 38 589 A1 4/1983

(Continued)

OTHER PUBLICATIONS

C.W. Akins et al., "Preservation of Interventricular Septal Function in Patients Having Coronary Artery Bypass Grafts Without Cardiopulmonary Bypass," American Heart Journal, vol. 107, No. 2 Feb. 1984, pp. 304-309.

(Continued)

*Primary Examiner* — Charles A Marmor, II
*Assistant Examiner* — Catherine E Burk
(74) *Attorney, Agent, or Firm* — Law Office of Alan W. Cannon (57) ABSTRACT

Devices and methods for stabilizing tissue within a patient's body. Such a device is adapted to assume a reduced configuration and an operating configuration. The device assumes the reduced configuration for passage through a small opening to deliver a working end of the device to a site of the tissue to be stabilized. Such a device may include first and second contact members that are mounted for rotation, with each having a contact surface adapted to contact a surface of the tissue. When the device is in the operating configuration, a largest cross-sectional dimension of the contact members may be greater than a largest dimension of an opening through which the contact members were passed. However, when in the reduced configuration, largest cross-sectional dimension of the contact members is less than the largest dimension of the opening.

33 Claims, 7 Drawing Sheets

U.S. PATENT DOCUMENTS

| | | |
|---|---|---|
| 3,782,387 A | 1/1974 | Falabella |
| 3,783,873 A | 1/1974 | Jacobs |
| 3,807,406 A | 4/1974 | Rafferty et al. |
| 3,858,926 A | 1/1975 | Ottenhues |
| 3,882,855 A | 5/1975 | Schulte et al. |
| 3,912,317 A | 10/1975 | Ohnaka |
| 3,916,909 A | 11/1975 | Kletschka et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,049,484 A | 9/1977 | Priest et al. |
| 4,052,980 A | 10/1977 | Grams et al. |
| 4,094,484 A | 6/1978 | Galione et al. |
| 4,096,853 A | 6/1978 | Weigand |
| 4,096,864 A | 6/1978 | Kletschka et al. |
| 4,185,636 A | 1/1980 | Gabbay et al. |
| 4,217,890 A | 8/1980 | Owens |
| 4,226,228 A | 10/1980 | Shin et al. |
| 4,230,119 A | 10/1980 | Blum |
| 4,300,541 A | 11/1981 | Burgin |
| 4,300,564 A | 11/1981 | Furihata |
| 4,306,561 A | 12/1981 | de Medinaceli |
| 4,350,160 A | 9/1982 | Kolesov et al. |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,597,382 A | 7/1986 | Perez, Jr. et al. |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| 4,708,510 A | 11/1987 | McConnell et al. |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,394 A | 5/1988 | Watanabe |
| 4,747,395 A | 5/1988 | Brief |
| 4,754,746 A | 7/1988 | Cox |
| 4,787,662 A | 11/1988 | Dewez |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,904,012 A | 2/1990 | Nishiguchi et al. |
| 4,925,443 A | 5/1990 | Heilman et al. |
| 4,931,341 A | 6/1990 | Haffer et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,566 A | 2/1991 | Shulman et al. |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,098,432 A | 3/1992 | Wagenknecht et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,192,070 A | 3/1993 | Nagai et al. |
| 5,196,003 A | 3/1993 | Bilweis |
| 5,231,974 A | 8/1993 | Giglio et al. |
| 5,256,132 A | 10/1993 | Snyders |
| 5,268,640 A | 12/1993 | Du et al. |
| 5,287,861 A | 2/1994 | Wilk |
| 5,290,082 A | 3/1994 | Palmer et al. |
| 5,293,863 A | 3/1994 | Zhu et al. |
| 5,300,087 A | 4/1994 | Knoepfler |
| 5,306,234 A | 4/1994 | Johnson |
| 5,318,013 A | 6/1994 | Wilk |
| 5,336,252 A | 8/1994 | Cochen |
| 5,339,801 A | 8/1994 | Poloyko et al. |
| 5,348,259 A | 9/1994 | Blanco et al. |
| 5,363,841 A | 11/1994 | Coker |
| 5,363,882 A | 11/1994 | Chikama |
| 5,370,685 A | 12/1994 | Stevens |
| 5,375,588 A | 12/1994 | Yoon |
| 5,381,788 A | 1/1995 | Matula et al. |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,433,700 A | 7/1995 | Peters |
| 5,437,651 A | 8/1995 | Todd et al. |
| 5,452,733 A | 9/1995 | Sterman et al. |
| 5,453,078 A | 9/1995 | Valentine et al. |
| 5,467,763 A | 11/1995 | McMahon et al. |
| 5,480,425 A | 1/1996 | Ogilive |
| 5,484,391 A | 1/1996 | Buckman, Jr. et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,513,827 A | 5/1996 | Michelson |
| 5,514,075 A | 5/1996 | Moll et al. |
| 5,514,076 A | 5/1996 | Ley |
| 5,520,609 A | 5/1996 | Moll et al. |
| 5,520,610 A | 5/1996 | Giglio et al. |
| 5,522,819 A | 6/1996 | Graves et al. |
| 5,529,571 A | 6/1996 | Daniel |
| 5,536,251 A | 7/1996 | Evard et al. |
| 5,547,458 A | 8/1996 | Ortiz et al. |
| 5,554,101 A | 9/1996 | Matula et al. |
| RE35,352 E | 10/1996 | Peters |
| 5,564,682 A | 10/1996 | Tsuji |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,578,061 A | 11/1996 | Stroetmann et al. |
| 5,582,580 A | 12/1996 | Buckman, Jr. et al. |
| 5,584,803 A | 12/1996 | Stevens et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,613,950 A | 3/1997 | Yoon |
| 5,632,746 A | 5/1997 | Middleman et al. |
| 5,651,378 A | 7/1997 | Metheny et al. |
| 5,662,300 A | 9/1997 | Michelson |

| | | | | | | |
|---|---|---|---|---|---|---|
| 5,667,480 | A | 9/1997 | Knight et al. | D421,803 | S | 3/2000 | Koros et al. |
| 5,707,362 | A | 1/1998 | Yoon | 6,032,672 | A | 3/2000 | Taylor |
| 5,713,951 | A | 2/1998 | Garrison et al. | 6,033,362 | A | 3/2000 | Cohn |
| 5,722,935 | A | 3/1998 | Christian | 6,036,641 | A | 3/2000 | Taylor et al. |
| 5,727,569 | A | 3/1998 | Benetti et al. | 6,042,539 | A | 3/2000 | Harper et al. |
| 5,728,151 | A | 3/1998 | Garrison et al. | 6,042,607 | A | 3/2000 | Williamson, IV et al. |
| 5,730,757 | A | 3/1998 | Benetti et al. | 6,050,266 | A | 4/2000 | Benetti et al. |
| 5,735,290 | A | 4/1998 | Sterman et al. | 6,063,021 | A | 5/2000 | Hossain et al. |
| 5,749,892 | A | 5/1998 | Vierra et al. | 6,066,160 | A | 5/2000 | Colvin et al. |
| 5,755,660 | A | 5/1998 | Tyagi | 6,071,235 | A | 6/2000 | Furnish et al. |
| 5,755,682 | A | 5/1998 | Knudson | 6,071,295 | A | 6/2000 | Takahashi |
| 5,766,151 | A | 6/1998 | Valley et al. | 6,074,343 | A | 6/2000 | Nathanson et al. |
| 5,772,583 | A | 6/1998 | Wright et al. | 6,099,468 | A | 8/2000 | Santilli et al. |
| 5,782,746 | A | 7/1998 | Wright | 6,102,853 | A | 8/2000 | Scirica et al. |
| 5,782,813 | A | 7/1998 | Yoon | 6,102,854 | A | 8/2000 | Carfier et al. |
| 5,789,661 | A | 8/1998 | Fauque et al. | 6,110,187 | A | 8/2000 | Donlon |
| 5,795,291 | A | 8/1998 | Koros et al. | 6,120,436 | A | 9/2000 | Anderson et al. |
| 5,797,960 | A | 8/1998 | Stevens et al. | 6,132,370 | A | 10/2000 | Furnish et al. |
| 5,799,661 | A | 9/1998 | Boyd et al. | 6,139,492 | A | 10/2000 | Vierra et al. |
| 5,803,902 | A | 9/1998 | Sienkiewicz et al. | 6,149,583 | A | 11/2000 | Vierra et al. |
| 5,807,243 | A | 9/1998 | Vierra et al. | 6,152,874 | A | 11/2000 | Looney et al. |
| 5,813,410 | A | 9/1998 | Levin | 6,159,201 | A | 12/2000 | Hamilton et al. |
| 5,818,231 | A | 10/1998 | Smith | 6,159,231 | A | 12/2000 | Looney et al. |
| 5,820,555 | A | 10/1998 | Watkins, III et al. | 6,183,486 | B1 | 2/2001 | Snow et al. |
| 5,836,311 | A | 11/1998 | Borst et al. | 6,190,311 | B1 | 2/2001 | Glines et al. |
| 5,846,187 | A | 12/1998 | Wells et al. | 6,193,652 | B1 | 2/2001 | Berky et al. |
| 5,846,193 | A | 12/1998 | Wright et al. | 6,193,732 | B1 | 2/2001 | Frantzen et al. |
| 5,846,194 | A | 12/1998 | Wasson et al. | 6,199,556 | B1 | 3/2001 | Benetti et al. |
| 5,864,275 | A | 1/1999 | Ohashi et al. | 6,200,263 | B1 | 3/2001 | Person |
| 5,865,730 | A | 2/1999 | Fox et al. | 6,210,323 | B1 | 4/2001 | Gilhuly et al. |
| 5,868,770 | A | 2/1999 | Rygaard | 6,213,940 | B1 | 4/2001 | Sherts et al. |
| 5,871,489 | A | 2/1999 | Ovil | 6,213,941 | B1 | 4/2001 | Benetti et al. |
| 5,875,782 | A | 3/1999 | Ferrari et al. | 6,224,545 | B1 | 5/2001 | Cocchia et al. |
| 5,876,332 | A | 3/1999 | Looney | 6,228,068 | B1 | 5/2001 | Yoon |
| 5,879,291 | A | 3/1999 | Kolata et al. | 6,231,506 | B1 | 5/2001 | Hu et al. |
| 5,879,371 | A | 3/1999 | Gardiner et al. | 6,231,585 | B1 | 5/2001 | Takahashi et al. |
| 5,882,299 | A | 3/1999 | Rastegar et al. | 6,251,065 | B1 | 6/2001 | Kochamba |
| 5,882,345 | A | 3/1999 | Yoon | 6,254,535 | B1 | 7/2001 | Furnish et al. |
| 5,885,271 | A | 3/1999 | Hamilton et al. | 6,264,605 | B1 | 7/2001 | Scirica et al. |
| 5,888,247 | A | 3/1999 | Benetti | 6,283,912 | B1 | 9/2001 | Hu et al. |
| 5,891,017 | A | 4/1999 | Swindle et al. | 6,290,644 | B1 | 9/2001 | Green et al. |
| 5,894,843 | A | 4/1999 | Benetti et al. | 6,308,104 | B1 | 10/2001 | Taylor et al. |
| 5,899,425 | A | 5/1999 | Corey, Jr. et al. | 6,315,717 | B1 | 11/2001 | Benetti et al. |
| 5,906,607 | A | 5/1999 | Taylor et al. | 6,328,688 | B1 | 12/2001 | Borst et al. |
| 5,908,378 | A | 6/1999 | Kovacs et al. | 6,331,157 | B2 | 12/2001 | Hancock |
| 5,908,382 | A | 6/1999 | Koros | 6,331,158 | B1 | 12/2001 | Hu et al. |
| 5,913,876 | A | 6/1999 | Taylor et al. | 6,332,468 | B1 | 12/2001 | Benetti |
| 5,921,979 | A | 7/1999 | Kovacs et al. | 6,334,843 | B1 | 1/2002 | Borst et al. |
| 5,924,424 | A | 7/1999 | Stevens et al. | 6,336,898 | B1 | 1/2002 | Borst et al. |
| 5,927,284 | A | 7/1999 | Borst et al. | 6,338,710 | B1 | 1/2002 | Takahashi et al. |
| 5,944,658 | A | 8/1999 | Koros et al. | 6,338,712 | B2 | 1/2002 | Spence et al. |
| 5,944,736 | A | 8/1999 | Taylor et al. | 6,346,077 | B1 | 2/2002 | Taylor et al. |
| 5,947,125 | A | 9/1999 | Benetti | 6,348,036 | B1 | 2/2002 | Looney et al. |
| 5,947,896 | A | 9/1999 | Sherts et al. | 6,350,229 | B1 | 2/2002 | Borst et al. |
| 5,957,832 | A | 9/1999 | Taylor et al. | 6,355,028 | B2 | 3/2002 | Castaneda et al. |
| 5,957,835 | A | 9/1999 | Anderson et al. | 6,361,493 | B1 | 3/2002 | Spence et al. |
| 5,961,481 | A | 10/1999 | Sterman et al. | 6,364,826 | B1 | 4/2002 | Borst et al. |
| 5,967,972 | A | 10/1999 | Santilli et al. | 6,371,906 | B1 | 4/2002 | Borst et al. |
| 5,967,973 | A | 10/1999 | Sherts et al. | 6,371,910 | B1 | 4/2002 | Zwart et al. |
| 5,972,030 | A | 10/1999 | Garrison et al. | 6,375,611 | B1 | 4/2002 | Voss et al. |
| 5,976,069 | A | 11/1999 | Navia et al. | 6,379,297 | B1 * | 4/2002 | Furnish et al. ................. 600/213 |
| 5,976,080 | A | 11/1999 | Farascioni et al. | 6,390,976 | B1 | 5/2002 | Spence et al. |
| 5,976,171 | A | 11/1999 | Taylor et al. | 6,394,948 | B1 | 5/2002 | Borst et al. |
| 5,984,864 | A | 11/1999 | Fox et al. | 6,394,951 | B1 | 5/2002 | Taylor et al. |
| 5,984,865 | A | 11/1999 | Farley et al. | 6,395,026 | B1 | 5/2002 | Aboul-Hosn et al. |
| 5,984,867 | A | 11/1999 | Deckman et al. | 6,398,726 | B1 | 6/2002 | Romans et al. |
| 5,984,959 | A | 11/1999 | Robertson et al. | 6,406,424 | B1 | 6/2002 | Williamson et al. |
| 6,007,486 | A | 12/1999 | Hunt et al. | 6,436,107 | B1 | 8/2002 | Wang et al. |
| 6,007,523 | A | 12/1999 | Mangosong | 6,447,443 | B1 | 9/2002 | Keogh et al. |
| 6,010,531 | A | 1/2000 | Donlon et al. | 6,458,079 | B1 | 10/2002 | Cohn et al. |
| 6,013,027 | A | 1/2000 | Khan et al. | 6,464,629 | B1 | 10/2002 | Boone et al. |
| 6,015,378 | A | 1/2000 | Borst et al. | 6,464,630 | B1 | 10/2002 | Borst et al. |
| 6,015,382 | A | 1/2000 | Zwart et al. | 6,464,690 | B1 * | 10/2002 | Castaneda et al. ................. 606/1 |
| 6,015,427 | A | 1/2000 | Mueller et al. | 6,468,265 | B1 | 10/2002 | Evans et al. |
| 6,017,304 | A | 1/2000 | Vierra et al. | 6,471,644 | B1 | 10/2002 | Sidor, Jr. |
| 6,019,722 | A | 2/2000 | Spence et al. | 6,475,142 | B1 | 11/2002 | Parsons et al. |
| 6,027,476 | A | 2/2000 | Sterman et al. | 6,478,028 | B1 | 11/2002 | Paolitto et al. |
| 6,029,671 | A | 2/2000 | Stevens et al. | 6,478,029 | B1 | 11/2002 | Boyd et al. |
| 6,030,340 | A | 2/2000 | Maffei et al. | 6,478,728 | B1 | 11/2002 | Wright |

| | | |
|---|---|---|
| 6,478,729 B1 | 11/2002 | Rogers et al. |
| 6,478,734 B1 | 11/2002 | Taylor et al. |
| 6,482,151 B1 | 11/2002 | Vierra et al. |
| 6,494,211 B1 | 12/2002 | Boyd et al. |
| 6,500,170 B2 | 12/2002 | Palmer et al. |
| 6,503,245 B2* | 1/2003 | Palmer et al. ............ 606/1 |
| 6,506,149 B2 | 1/2003 | Peng et al. |
| 6,511,416 B1 | 1/2003 | Green, II et al. |
| 6,537,212 B2 | 3/2003 | Sherts et al. |
| 6,554,823 B2 | 4/2003 | Palmer et al. |
| 6,565,508 B2 | 5/2003 | Scirica et al. |
| 6,579,281 B2 | 6/2003 | Palmer et al. |
| 6,582,420 B2 | 6/2003 | Castaneda et al. |
| 6,587,750 B2 | 7/2003 | Gerbi et al. |
| 6,589,166 B2 | 7/2003 | Knight et al. |
| 6,592,573 B2 | 7/2003 | Castaneda et al. |
| 6,599,240 B2 | 7/2003 | Puchovsky et al. |
| 6,602,189 B1 | 8/2003 | Bennetti et al. |
| 6,607,478 B2 | 8/2003 | Williams |
| 6,607,479 B1 | 8/2003 | Kochamba et al. |
| 6,610,008 B1 | 8/2003 | Spence et al. |
| 6,610,009 B2 | 8/2003 | Person |
| 6,613,039 B1 | 9/2003 | Namba |
| 6,620,173 B2 | 9/2003 | Gerbi et al. |
| 6,626,830 B1 | 9/2003 | Califiore et al. |
| 6,626,930 B1 | 9/2003 | Allen et al. |
| 6,644,319 B1 | 11/2003 | Benetti |
| 6,652,454 B2 | 11/2003 | Hu et al. |
| 6,656,113 B2 | 12/2003 | Green, II et al. |
| 6,659,939 B2 | 12/2003 | Moll et al. |
| 6,663,645 B2 | 12/2003 | Nishtala et al. |
| 6,673,013 B2 | 1/2004 | Benetti et al. |
| 6,685,632 B1 | 2/2004 | Hu et al. |
| 6,689,054 B2 | 2/2004 | Furnish et al. |
| 6,695,868 B2 | 2/2004 | Looney et al. |
| 6,699,177 B1 | 3/2004 | Wang et al. |
| 6,701,930 B2 | 3/2004 | Benetti et al. |
| 6,702,732 B1* | 3/2004 | Lau et al. .............. 600/37 |
| 6,705,988 B2 | 3/2004 | Spence et al. |
| 6,726,622 B2 | 4/2004 | Spence et al. |
| 6,730,020 B2 | 5/2004 | Peng et al. |
| 6,736,774 B2 | 5/2004 | Benetti et al. |
| 6,740,028 B2 | 5/2004 | Boone et al. |
| 6,743,169 B1 | 6/2004 | Taylor et al. |
| 6,743,170 B1 | 6/2004 | Spence et al. |
| 6,746,467 B1 | 6/2004 | Taylor et al. |
| 6,755,780 B2 | 6/2004 | Borst et al. |
| 6,758,808 B2 | 7/2004 | Paul et al. |
| 6,764,445 B2 | 7/2004 | Ramans et al. |
| 6,817,972 B2 | 11/2004 | Snow |
| 6,821,247 B2 | 11/2004 | Vierra et al. |
| 6,849,044 B1 | 2/2005 | Voss et al. |
| 6,852,075 B1 | 2/2005 | Taylor |
| 6,893,391 B2 | 5/2005 | Taylor |
| 6,899,670 B2 | 5/2005 | Peng et al. |
| 6,936,001 B1 | 8/2005 | Snow |
| 7,025,722 B2 | 4/2006 | Vierra et al. |
| 7,217,240 B2 | 5/2007 | Snow |
| 7,250,028 B2* | 7/2007 | Julian et al. ............ 600/229 |
| 2001/0023311 A1* | 9/2001 | Snow ............ 600/37 |
| 2002/0082625 A1 | 6/2002 | Huxel et al. |
| 2002/0095139 A1* | 7/2002 | Keogh et al. ............ 606/1 |
| 2002/0120177 A1 | 8/2002 | Borst et al. |
| 2002/0124856 A1 | 9/2002 | Borst et al. |
| 2002/0161277 A1 | 10/2002 | Boone et al. |
| 2003/0060685 A1 | 3/2003 | Houser et al. |
| 2003/0078470 A1 | 4/2003 | Borst et al. |
| 2003/0158463 A1* | 8/2003 | Julian et al. ............ 600/104 |
| 2004/0082837 A1* | 4/2004 | Willis ............ 600/210 |
| 2004/0087834 A1 | 5/2004 | Benetti et al. |
| 2004/0092798 A1 | 5/2004 | Spence et al. |
| 2004/0092799 A1 | 5/2004 | Hu et al. |
| 2004/0143168 A1 | 7/2004 | Hu et al. |
| 2004/0176659 A1 | 9/2004 | Peng et al. |
| 2004/0225195 A1 | 11/2004 | Spence et al. |
| 2004/0236184 A1 | 11/2004 | Benetti et al. |
| 2005/0010197 A1 | 1/2005 | Lau et al. |
| 2005/0033111 A1 | 2/2005 | Taylor |
| 2005/0038316 A1 | 2/2005 | Taylor |

FOREIGN PATENT DOCUMENTS

| | | |
|---|---|---|
| DE | 90 04 513 | 6/1990 |
| DE | 41 39 695 A1 | 6/1993 |
| DE | 697 21 099 | 2/2004 |
| EP | 0 293 760 A3 | 12/1988 |
| EP | 0 293 760 B1 | 12/1988 |
| EP | 0 630 629 A1 | 5/1994 |
| EP | 0 668 058 A1 | 2/1995 |
| EP | 0 792 620 A2 | 2/1997 |
| EP | 0 792 620 A3 | 2/1997 |
| EP | 0 792 620 B1 | 2/1997 |
| EP | 0 803 228 A1 | 4/1997 |
| EP | 0 820 721 A1 | 7/1997 |
| EP | 0 791 329 A1 | 8/1997 |
| EP | 0 791 330 A2 | 8/1997 |
| EP | 0 808 606 A1 | 11/1997 |
| EP | 0 919 193 A1 | 10/1998 |
| EP | 0 993 806 A2 | 9/1999 |
| GB | 473.451 | 0/1915 |
| GB | 168216 | 9/1921 |
| GB | 2 233 561 A | 1/1991 |
| GB | 2 267 827 A | 12/1993 |
| SU | 938967 | 7/1982 |
| US | 938967 | 7/1982 |
| WO | WO 87/04081 | 7/1987 |
| WO | WO 88/00481 | 1/1988 |
| WO | WO 93/09720 | 5/1993 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 96/32882 | 10/1996 |
| WO | WO 96/40354 | 12/1996 |
| WO | WO 97/10753 | 3/1997 |
| WO | WO 97/26828 | 7/1997 |
| WO | WO 97/32514 | 9/1997 |
| WO | WO 97/40738 | 11/1997 |
| WO | WO 97/40752 | 11/1997 |
| WO | WO 98/17182 | 4/1998 |
| WO | WO 98/27869 | 7/1998 |
| WO | WO 98/48703 | 11/1998 |
| WO | WO 98/49944 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/16367 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |
| WO | WO 00/66008 | 9/2000 |
| WO | WO 01/15607 A1 | 3/2001 |
| WO | WO 01/17437 A2 | 3/2001 |
| WO | WO 01/17437 A3 | 3/2001 |
| WO | WO 01/58362 A1 | 8/2001 |

OTHER PUBLICATIONS

Angelini, G.D., M.D. et al., "A Fiber-Optic Retractor for Harvesting the Internal Mammary Artery," Ann. Thorac. Surg. (1990; 50:314-5).

Angelini, G.D., M.D., "A Simple, Inexpensive Method of Heart Retraction During Coronary Artery Bypass Surgery," Ann. Thora. Surg 46:46-247, Aug. 1988.

Anstadt, M.P. MD et al., "Direct Mechanical Ventricular Actuation for Cardiac Arrest in Humans," Chest, vol. 100, No. 1, Jul. 1991, pp. 86-92.

Mehlhaff, Marlene, New Heart Procedure Arrive. Nov. 20, 1997.

Pittman, John, M.D., et al., "Improved Visualization of the Internal Mammary Artery with a New Retractor System," Ann. Thorac. Surg., 1989; 48:869-70.

* cited by examiner

SURGICAL STABILIZERS AND METHODS FOR USE IN REDUCED-ACCESS SURGICAL SITES

FIELD OF THE INVENTION

The present invention pertains to the field of surgical instruments and techniques, and more particularly to surgical instruments and techniques for use in reduced or restricted working spaces.

BACKGROUND OF THE INVENTION

Certain surgical procedures require the surgeon to perform delicate surgical operations on tissues within the body that are moving or otherwise unstable. The ability to stabilize or immobilize a surgical site provides greatly improved surgical accuracy and precision and reduces the time required to complete a particular procedure. A large and growing number of surgeons are performing successful coronary artery bypass graft (CABG) surgery on the beating heart by temporarily stabilizing or immobilizing a localized area of the beating heart. Methods and apparatus for performing a CABG procedure on a beating heart are described in U.S. Pat. Nos. 5,894,843 and 5,727,569 to Benetti et al., both of which are incorporated herein, in their entireties, by reference thereto.

In a typical CABG procedure, a blocked or restricted section of coronary artery, which normally supplies blood to some portion of the heart, is bypassed using a source vessel or graft vessel to re-establish blood flow to the artery downstream of the blockage. This procedure requires the surgeon to create a fluid connection, or anastomosis, between the source or graft vessel and an arteriotomy or incision in the coronary artery. Forming an anastomosis between two vessels in this manner is a particularly delicate procedure requiring the precise placement of tiny sutures in the tissue surrounding the arteriotomy in the coronary artery and the source or graft vessel.

The rigors of creating a surgical anastomosis between a coronary artery and a source vessel or graft vessel demands that the target site for the anastomosis be substantially motionless. To this end, a number of devices have been developed which are directed to stabilizing a target site on the beating heart for the purpose of completing a cardiac surgical procedure, such as completing an anastomosis. Stabilization may be provided using a device that provides a mechanical or compression force to the tissue or by a device which applies a negative pressure or suction to the tissue. Representative devices useful for stabilizing a beating heart are described, for example, in U.S. Pat. Nos. 5,894,843; 5,727,569; 5,836,311 and 5,865,730, each of which is incorporated herein, in its entirety, by reference thereto.

As beating heart procedures have evolved, regardless of whether compression or negative pressure has been used to stabilize or immobilize the heart, new challenges have arisen. For example, surgeons may gain access to the heart using a number of different approaches, both open and closed chest, such as through a sternotomy, mini-sternotomy, thoracotomy or mini-thoracotomy, or less invasively through a port provided within the chest cavity of the patient, e.g., between the ribs or in a subxyphoid area, with or without the visual assistance of a thoracoscope. Accordingly, the devices used to stabilize the heart must be configured to accommodate the particular approach chosen. For example, when a closed chest approach is used such as a port access approach wherein the device is introduced into the body cavity through a small access port or stab wound, the device must be designed to be advanced through such small openings without damaging the device or any internal body structures. A continuing need remains for new and better instruments that are capable of being delivered through small openings and still function satisfactorily in a closed-chest environment.

Furthermore, in addition to addressing delivery problems of instruments though small access openings, the working space within a closed-chest surgical environment is extremely limited, allowing much less room to maneuver the instruments, as compared to the space provided in an open-chest surgical site, once they have been successfully delivered or placed in the operative site. Thus, new and better approaches, tools and techniques for controlling instruments in a closed chest environment are needed.

As such, there is continued interest in the development of new devices and methods for easily and effectively stabilizing or immobilizing tissue, e.g., a beating heart, in a limited space environment, such as occurs during closed-chest procedures. Of particular interest would be the development of such devices and methods of use which may be used in a variety of surgical approaches, including a sternotomy, mini-sternotomy, thoracotomy, mini-thoracotomy, transabdominal entry, and particularly in less invasive techniques such as endoscopic or port access procedures (e.g., between the ribs or in a subxyphoid area), with or without the visual assistance of a thoracoscope. Similar interest exists for the development of devices that are operable in other reduced-access surgical environments within a patient.

SUMMARY OF THE INVENTION

Devices and methods are provided for stabilizing tissue within a patient's body, wherein such a device is adapted to assume a reduced configuration and an operating configuration. The device assumes the reduced configuration for passage through a small opening to deliver a working end of the device to a site of the tissue to be stabilized. Such a device may comprise a base member, and first and second contact members extending distally from the base member, wherein the contact members are mounted for rotation with respect to said base member. The contact members each have a contact surface adapted to contact a surface of the tissue. When the device is in the operating configuration, the contact surfaces face in a direction to contact the tissue. When the device is in the reduced configuration, the contact members have been rotated with respect to one another so that the contact surfaces substantially face one another.

Devices and methods for stabilizing tissue within a patient's body are provided, wherein such a device is adapted to assume a reduced configuration for passage through a small opening to deliver a working end of the device to a site of the tissue to be stabilized. The device includes first and second contact members extending from a base member, and wherein the contact members are mounted for rotation with respect to the base member. The contact members each have a contact surface adapted to contact a surface of the tissue. The contact members are configured to assume a reduced configuration and an operating configuration. When the contact members are in the operating configuration, the contact surfaces face in a direction to contact the tissue. When the contact members are in the reduced configuration, the contact members have been rotated with respect to one another so that the contact surfaces substantially face one another. The arm may be configured to assume an unlocked configuration and a locked configuration, wherein the arm is adjustable relative to the contact members when in the unlocked configuration, and wherein the arm is fixed relative to the contact members when in the locked configuration. A locking member may be provided which is configured to facilitate locking of the arm, wherein upon locking the arm in the locked configuration, the contact members are also locked against rotation with respect to the base member.

A method of stabilizing tissue is provided to include the steps of: providing a stabilizing device having contact members configured to assume a reduced configuration and an operating configuration; positioning the contact members in the reduced configuration; passing the contact members through an opening, wherein a largest cross-sectional dimension of the contact members in the reduced configuration is smaller than a largest cross-sectional dimension of the opening, and wherein a largest cross-sectional dimension of the contact members in the operating configuration is larger than the largest cross-sectional dimension of the opening; and contacting the tissue with the contact surfaces of the contact members, with the contact members in the operating configuration, wherein the contact members automatically move from the reduced configuration to the operating configuration upon exiting the opening.

Methods and devices are provided for manipulating a surgical instrument in a reduced-access surgical site, wherein the surgical device comprises a working end that, when in an operating configuration, has a largest cross-sectional dimension greater than a largest cross-sectional dimension of an opening provided in a patient. Such a device may be manipulated by withdrawing the device proximally in a direction out of the patient; contacting a portion of the working end against a perimeter of the opening, wherein the working end automatically collapses from the operating configuration to a reduced configuration, and wherein a largest cross-sectional dimension of the working end, in the reduced configuration, is smaller that the largest cross-sectional dimension of the opening; and removing the device from the surgical site by passing the working end in the reduced configuration through the opening.

These and other advantages and features of the invention will become apparent to those persons skilled in the art upon reading the details of the devices and methods as more fully described below.

DETAILED DESCRIPTION OF THE INVENTION

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a foot" includes a plurality of such feet and reference to "the biasing member" includes reference to one or more biasing members and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "open-chest procedure" refers to a surgical procedure wherein access for performing the procedure is provided by a full sternotomy, wherein the sternum is incised and the patient's ribs are separated using a sternal retractor to open the chest cavity for access thereto.

The term "closed-chest procedure" refers to a surgical procedure wherein access for performing the procedure is provided by one or more openings which are much smaller than the opening provided by an open-chest procedure, and wherein a traditional sternotomy is not performed. Closed-chest procedures may include those where access is provided by any of a number of different approaches, including mini-sternotomy, thoracotomy or mini-thoracotomy, or less invasively through a port provided within the chest cavity of the patient, e.g., between the ribs or in a subxyphoid area, with or without the visual assistance of a thoracoscope.

The term "reduced-access surgical site" refers to a surgical site or operating space that has not been opened fully to the environment for access by a surgeon. Thus, for example, closed-chest procedures are carried out in reduced-access surgical sites. Other procedures, including procedures outside of the chest cavity, such as in the abdominal cavity or other locations of the body, may be carried out as reduced access procedures in reduced-access surgical sites. For example, the surgical site may be accessed through one or more ports, cannulae, or other small opening(s). What is often referred to as endoscopic surgery is surgery carried out in a reduced-access surgical site.

As alluded to above, surgical procedures carried out on a patient by "closed-chest" procedures or in "reduced-access surgical sites" allow much less free space for the surgeon to work in than do more conventional "open-chest" or open-site surgical procedures such as those where access is gained through a sternotomy or an open abdominal cavity, for example. As such, the instruments used during reduced-access procedures must be as non-obstructive as possible and require only minimal amounts of space for their use. The present invention provides devices and methods that are useful for performing surgical procedures where working space is limited.

Figure 1:
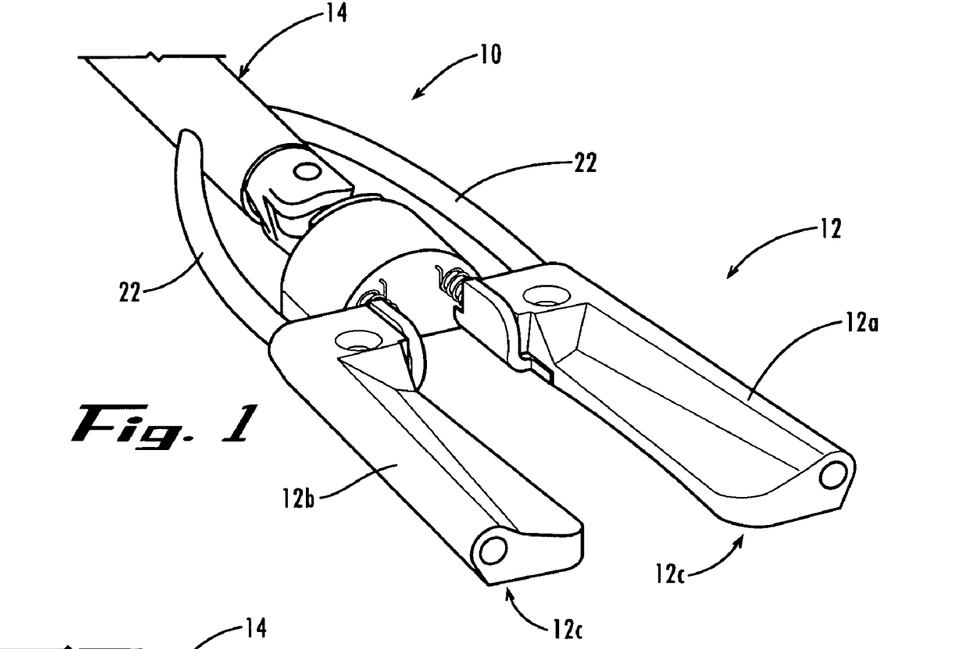
FIG. 1 is a partial perspective view of a stabilizer device according to the present invention.
Figure 2:
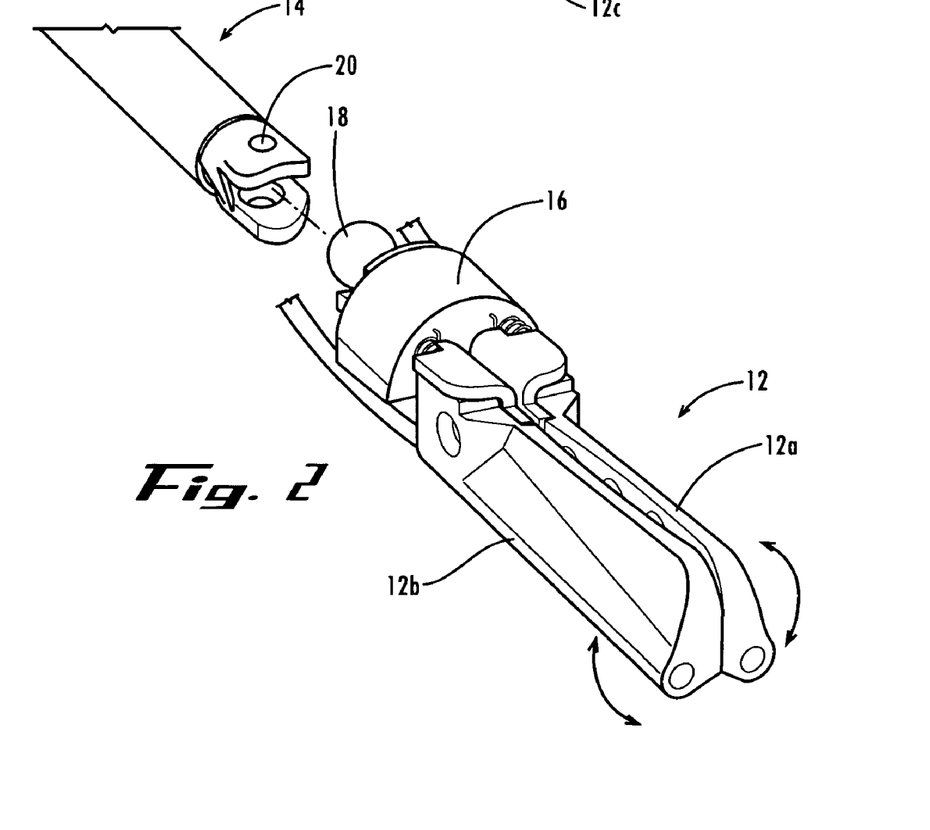
FIG. 2 is a partial perspective view of the device of FIG. 1, showing the working end in a reduced configuration.

FIG. 1 is a partial perspective view of a stabilizer device 10 having a distal working end or stabilizer foot 12 that is adapted to be temporarily reconfigured to have a reduced cross-section allowing it to be passed through a small port, obturator sleeve or other small opening that provides access to a reduced-access surgical site. FIG. 2 is a partial perspective view showing the stabilizer foot 12 in a reduced configuration wherein the cross-sectional area has been reduced. The reduced configuration is useful for passing the working end through a small opening. Support arm 14 is shown detached from working end 12. In some embodiments, support arm 14 is provided integrally with working end 12, while alternative embodiments, such as the one shown in FIGS. 1 and 2, allow support arm 14 to be removed and attached to working end 12 at will. With such a configuration, working end 12 may be passed through a small opening while support arm 14 is attached thereto, or may be passed through a small opening first, after which support arm 14 may be passed through the same or a different small opening and attached to the working end 12 including the stabilizer foot. Further detailed discussions of techniques for passing a stabilizer foot through a small opening and then subsequently passing a support arm through the same or a different small opening can be found in co-pending, commonly owned application Ser. No. 11/137,255, filed concurrently herewith (i.e., May 25, 2005) and titled "Surgical Instruments and Methods for Use in Reduced-Access Surgical Sites". Application Ser. No. 11/137,255 is hereby incorporated herein, in its entirety, by reference thereto.

Contact members 12a and 12b of the stabilizer foot extend distally and longitudinally from base 16 and are rotatably mounted thereto so as to be rotatable about longitudinal axes in the directions of the arrows shown. In the example shown in FIG. 2, a ball member 18 extends proximally from base 16 and is fixed with respect thereto. Support arm 14 may be provided with grasper jaws (operable from a proximal end thereof) or other socket type member 20 that is configured to mate with ball member 18. In a semi-fixed state, socket member 20 captures ball member 18 to prevent axial movement of stabilizer foot 12 with respect to support arm 14, while still allowing ball member 18 (and thus stabilizer foot 12) to rotate with respect to socket member 20 (and support arm 14). Upon increasing the compressive or clamping force of socket member 20 on ball member 18, stabilizer foot 12 becomes fixed with respect to support arm, so that it can neither rotate nor translate with respect to support arm 14. Examples of alternative connecting members that may be substituted for that described, for connecting support arm 14 with stabilizer foot 12, are described in application Ser. No. 11/137,255.

The example of FIGS. 1-2 utilizes suction or negative pressure to draw tissue into contact with contact members 12a,12b to accomplish stabilization of the tissue. At least one, typically a pair of suction lines 22 connect contact members 12a,12b with a source of negative pressure located proximally of device 10 and outside of the patient. Suction lines run generally along the contours of support arm 14, and may pass within the support arm 14 for embodiments where support arm 14 is tubular or otherwise has a conduit through which each suction line can be passed. Alternatively, suction lines 22 may closely follow the external contours of support arm 14.

A variety of alternative configurations may be employed for delivering negative pressure through contact members 12a,12b to deploy the negative pressure to the tissue surface through contact surfaces 12c, including, but not limited to, ports, open vacuum chambers or diffused vacuum chambers, each with or without a perimeter seal around each contact member or port, etc. Further detailed descriptions of vacuum configurations that may be employed in contact members 12a,12b are found in U.S. Pat. Nos. 6,032,672; 6,511,416; 6,406,424; 6,758,808, co-pending application Ser. No. 10/283,784 filed Oct. 29, 2002 and titled Tissue Stabilizer and Methods of Using the Same; and application Ser. No. 11/137,255, each of which is incorporated herein, in its entirety, by reference thereto.

Figure 3:
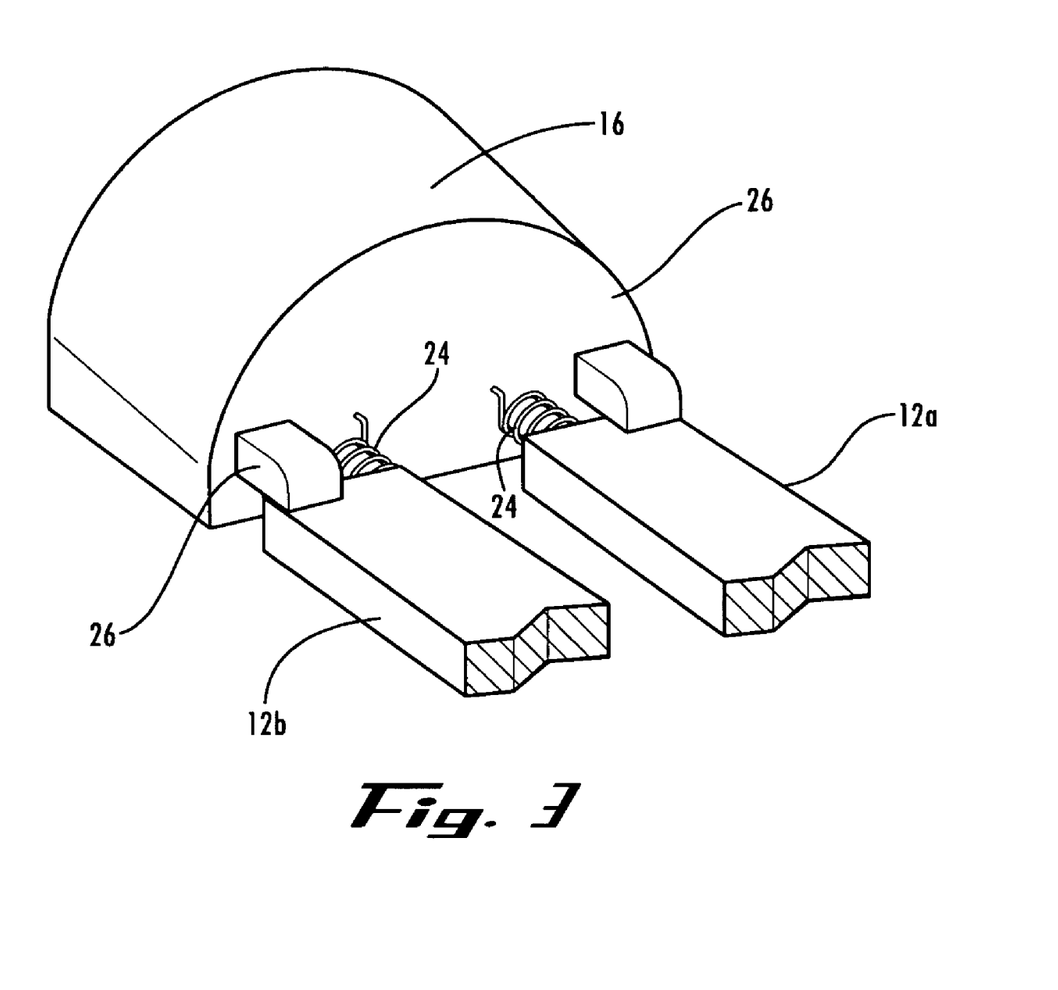
FIG. 3 is a partial view illustrating one example of a mechanism for rotating contact members of the device.

FIG. 3 is a partial view illustrating one example of a mechanism that permits the rotation of contact members 12a,12b as described. In this example, contact members 12a,12b are mounted to base 16, as shown, with biasing members 24 interconnecting base 16 with contact members 12a,12b, respectively. Although not shown in the example of FIG. 3, a shaft, axle or rod 27 may extend through each biasing member 24 to pivotally connect the contact members 12a,12b to base 16, respectively, to add axial rigidity to the working end. Shafts or rods 27 may be fixed with respect to one of base 16 and contact members 12a,12b or may be free to rotate with respect to both base 16 and contact members 12a,12b in the example of FIG. 3A. However, shafts or rods 27 must be free to rotate with at least one of base 16 and contact members 12a,12b to permit contact members 12a,12b to rotate with respect to base 16.

Biasing members 24 (such as torsion springs, leaf springs, or other members that can convert kinetic energy and store it as potential energy for later re-conversion to apply the energy as a spring force) retain less biasing force in the configuration shown in FIGS. 1 and 3 than in the configuration shown in FIG. 2. Thus, upon rotating contact members 12a,12b toward the collapsed configuration, the biasing force (stored potential energy) applied by biasing members 24 increases, so that when rotational forces on contacting members (such as restraint by a cannula or other delivery tube or mechanism, for example) 12a,12b is released, biasing members 24 drive contact members 21a,12b back to the operational configuration shown in FIGS. 1 and 3.

Stops 26 are provided to abut contact members 12a,12b when contact members 12a,12b have reached the fully expanded or operational configuration (FIGS. 1 and 3), thereby preventing over-rotation of contact members 12a, 12b, and retaining some potential energy in biasing members 24, so as to retain contact members 12a, 12b pressed against stops 26 with some positive biasing force. Stops 26 are fixed with respect to base 16 and may be formed as protrusions extending distally form base 16, as shown in FIG. 3. Biasing members 24 should retain sufficient biasing force or stored energy to maintain contact members 12a,12b abutted against stops 26 even in a situation where contact surfaces 12c are fixed to the tissue that is being stabilized and working end is lifted up to pull the tissue up slightly to increase tension at the location being stabilized. That is, contact members must be able to maintain the orientation of FIG. 3 (as held in position by biasing member 24) even while downward forces are applied to contact members 12a,12b resultant from lifting up on the device and lifting the tissue slightly.

Figure 4A:
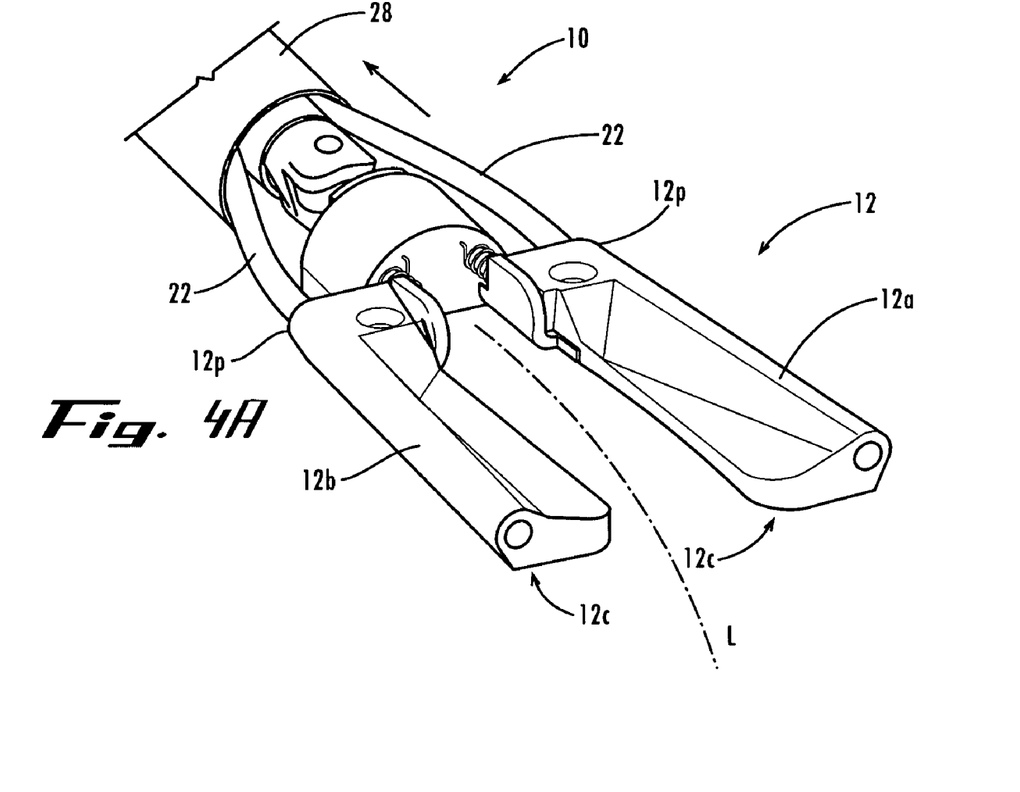
FIGS. 4A-4B illustrate an example of a manner in which a working end is configured to automatically collapse when pulled proximally through a small opening.
Figure 4B:
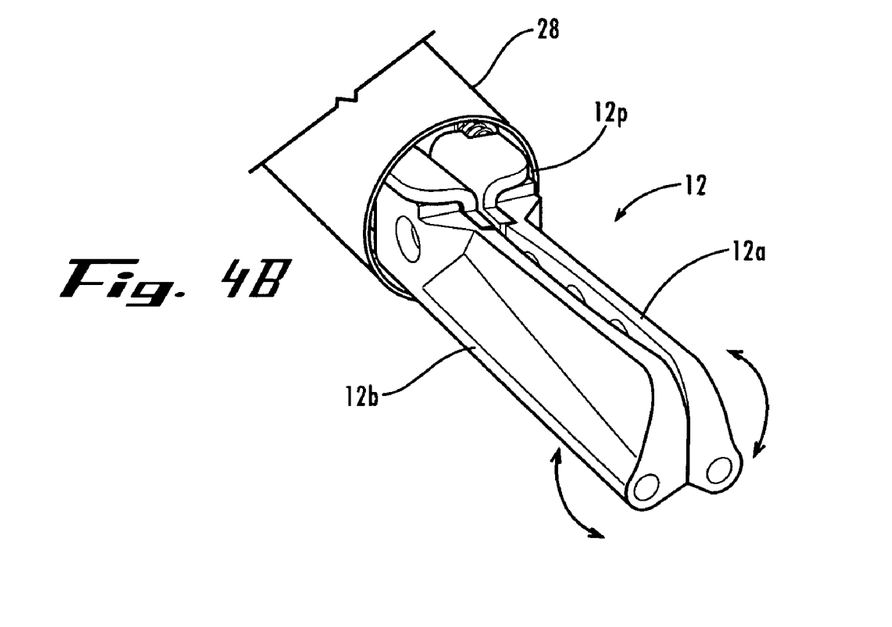

FIGS. 4A-4B illustrate an example of a manner in which working end 12 is configured to automatically collapse when pulled proximally through a small opening, such as an obturator sleeve, port or other small opening leading into a patient for example, such as a small thoracotomy, stab incision, etc. The proximal perimeters 12p of contact members 12a,12b may be tapered towards the central longitudinal axis L of foot 12, or otherwise shaped to facilitate collapsing to the position as shown in FIG. 2 as suction tubes 22 and contact members 12a,12b enter the small opening, such as the distal end of obturator sleeve 28 for example. As support arm 14 and suction tubes 22 are drawn into tube 28, suction tubes 22 are, of necessity, brought closer to one another by rubbing against the inside of tube 28 as base 16 gets closer and closer to the distal end of tube 28. As suction tubes 22 are brought closer together, this also rotates contact members 12a,12b against the biasing forces of biasing members 24, so that by the time the proximal ends of contact members 12a,12b meet the distal end of tube 28 (see FIG. 4B), they have been collapsed enough to be drawn into tube 28, at which time they become completely collapsed as they are drawn against the inner wall of tube 28, if they were not already completely collapsed by the time the proximal ends 12p meet with the distal end of tube 28.

Alternative to the use of suction for stabilizing tissue, a device as described herein may utilize mechanical force to provide a stabilization force to the tissue. In this type of arrangement, the contact surfaces 12c of the working end 12 may be provided as planar surfaces, or surfaces designed to substantially conform to a topology of the tissue surface in an area that is to be stabilized. Contact surfaces may include friction enhancing features, such as knurling or other roughened surface, or have a layer or coating that shows increased friction with the tissue to be stabilized relative to the material making up the remainder of contact members 12a,12b, or other friction enhancing features.

A variety of alternative configurations may be employed for delivering mechanical stabilizing forces through contact members 12a,12b. Further detailed descriptions of contact member configurations for mechanical stabilization that may be employed in contact members 12a,12b are found in U.S. Pat. Nos. 6,346,077; 6,331,158; 6,406,424; co-pending application Ser. No. 10/283,784; and application Ser. No. 11/137,255, each of which is incorporated herein, in its entirety, by reference thereto.

Figure 5:
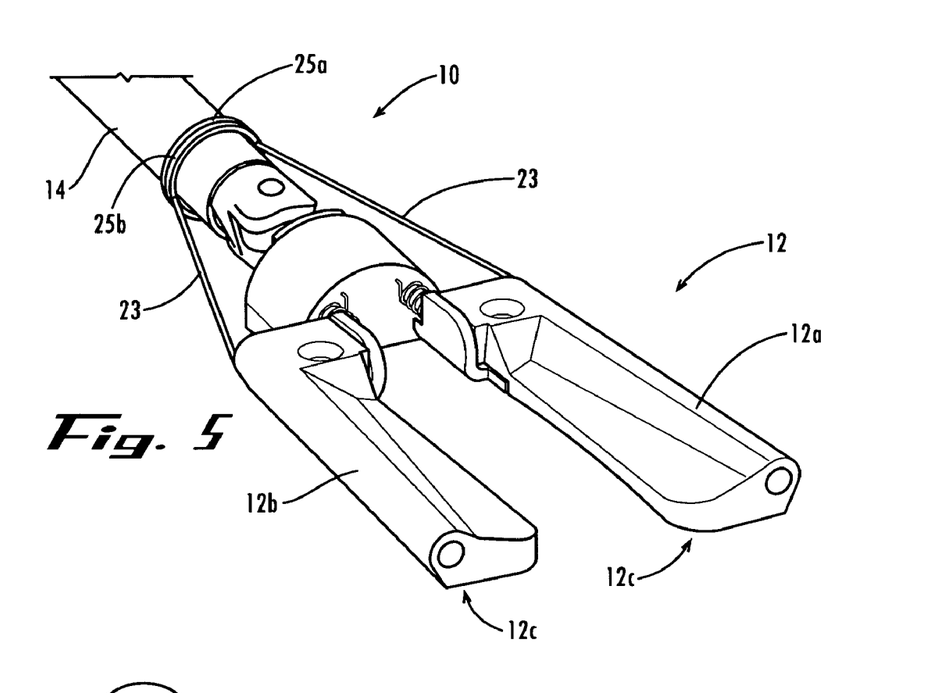
FIG. 5 illustrates an alternative configuration for automatically collapsing the working end.

Working ends 12 employing contact members 12a,12b that apply mechanical stabilizing forces, without the application of vacuum to the tissue, may also be constructed to move between an operational configuration and a collapsed or reduced cross-sectional area configuration, similar to that described above with regard to configurations that employ suction. FIG. 5 shows an example of a device 10 having feet 12a and 12b that apply mechanical forces to tissue contacted thereby to achieve stabilization. Working end 12 is in the operational configuration as shown in FIG. 5, but is also collapsible to a collapsed configuration. Feet 12a and 12b may be mounted to base 16 in any of the manners described above with regard to feet that apply suction. Similarly, FIG. 5 shows that rigid or semi-rigid rods, bars, wires, tubes or the like 23 may be fixed near the proximal periphery of feet 12a and 12b respectively, and joined to rings, sleeves or collars 25a,25b that are free to slide axially over support arm 14 and are also free to rotate with respect to one another. Accordingly, as feet 12a,12b are rotated to be placed in the collapsed configuration, rings 25a,25b rotate in opposite directions as driven by the rods 25a,25b to which they are respectively attached and which in turn are rotated in opposite directions by the rotation of feet 12a,12b from the operational configuration to the collapsed configuration. Upon release of the forces holding feet 12a,12b in the collapsed configuration, feet 12a,12b counter-rotate, as driven by biasing member 24 to reassume the operational configuration.

After use of device 10, when withdrawing the device through a small opening, tube 28 or the like, as the operator begins to withdraw device 10 proximally with respect to the tube or opening, pressure or force applied to rods 23 as they come into contact with the tube or opening causes rotation of rings 25a,25b and rotation of feet 12a,12b toward the collapsed configuration so that working end 12 can pass through the tube or opening for removal thereof. In order to initially insert working end 12 into a small opening, the operator may manually collapse feet 12a,12b by rotating them towards one another and then inserting the collapsed feet 12a,12b into the opening.

Figure 6A:
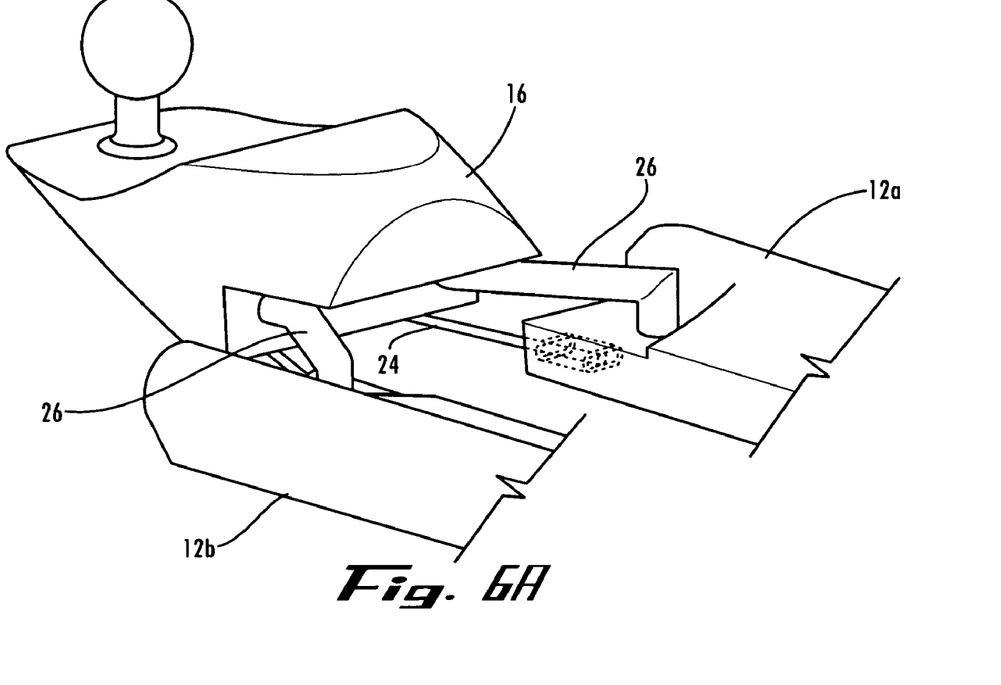
FIG. 6A is a partial perspective view of another example of a device according to the present invention.
Figure 6B:
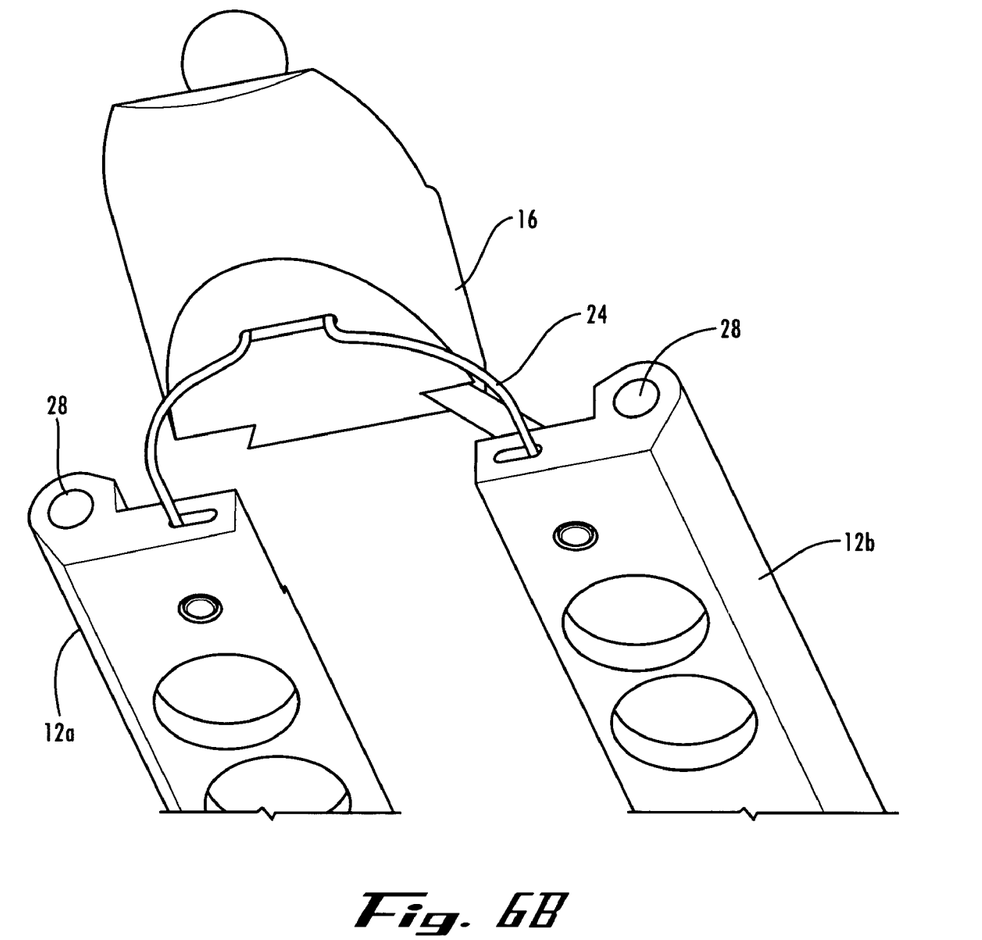
FIG. 6B is a partial bottom view of the device of FIG. 6A.

FIGS. 6A-6B are partial views illustrating another example of a mechanism that permits the rotation of contact members 12a,12b. Additionally, the configuration in FIGS. 6A-6B permits the tilting of the contact members 12a,12b to align them with base 16 (and optionally arm 14, when attached), to configure the device to be passed through a small opening, such as tube 28 or other small opening, as described. In this example, contact members 12a,12b are mounted to base 16, as shown, with biasing member 24 interconnecting base 16 with contact members 12a, 12b, respectively.

Figure 6C:
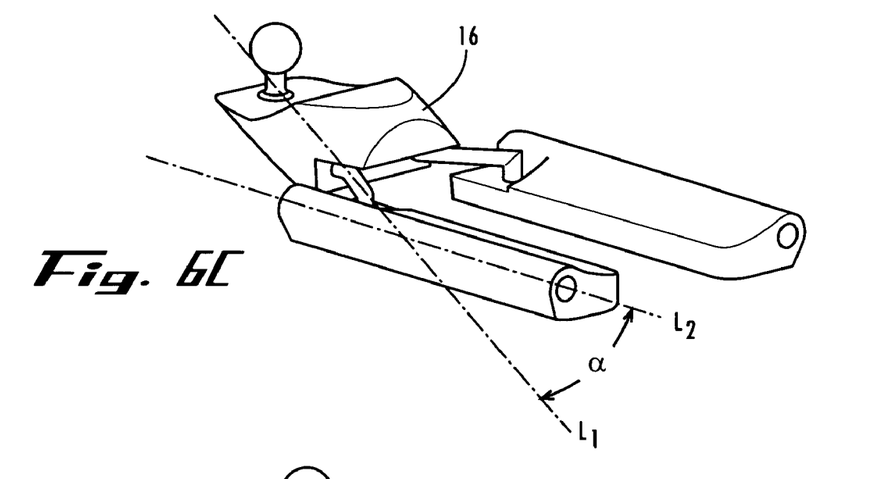
FIGS. 6C, 6D and 6E are progressive partial views showing movement of the working end from an operating configuration to a reduced configuration.

Biasing member 24 may be a pair of elastically deformable members, or typically, may be a single elastically deformable member such as a wire preformed from spring steel into the shape shown in FIG. 6B, leaf spring(s), or the like. In the least biased or operational configuration, biasing member is oriented as shown in FIG. 6B and orients contact members 12a,12b in the open or operational configuration shown. The open or operational configuration includes not only rotating contact members 12a,12b such that their contact surfaces face substantially in the same direction, but also tilting the contact members 12a12b such that they remain substantially parallel with one another, but form an angle with a longitudinal axis of the overall device 10, as shown in FIG. 6C. That is, contact members 12a,12b are tilted such that a longitudinal axis $L_2$ of contact members 12a,12b forms an angle α with a longitudinal axis $L_1$ of device 10 greater than 0 degrees and less than 90 degrees, more typically ranging from about 10 degrees to about 40 degrees., even more typically from about 20 degrees to about 35 degrees.

Figures 6D, 6E:
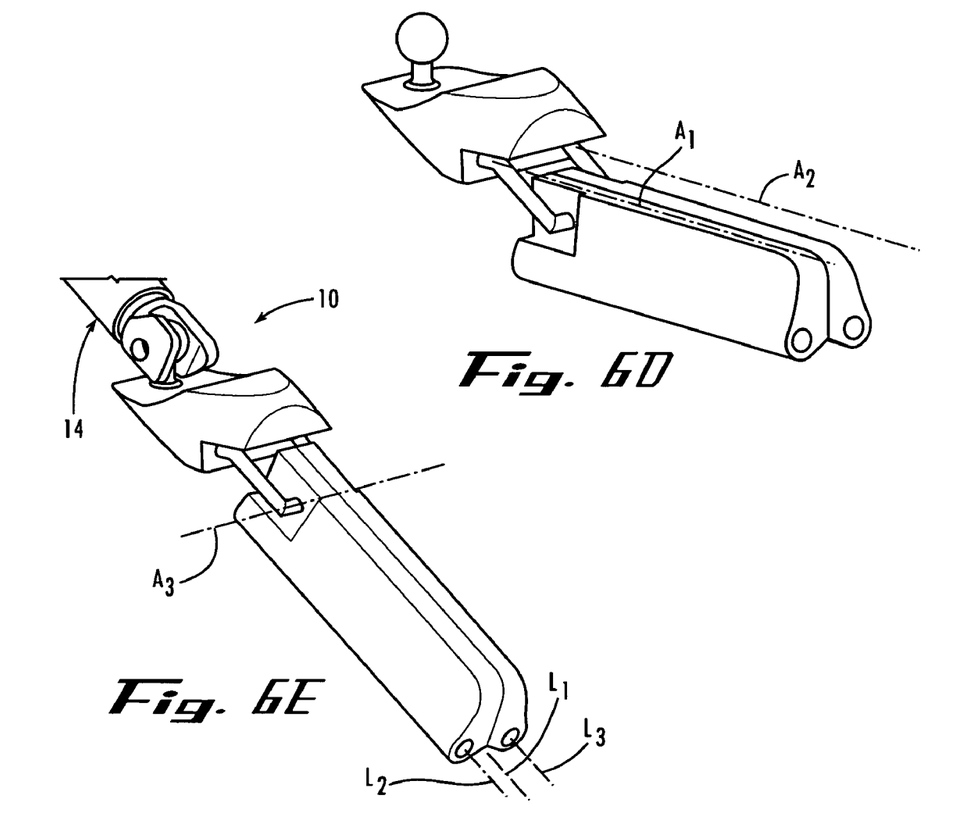

Biasing member 24 may be movable mounted in a slot or space 26 that permits movement of biasing members 24 (or portions of biasing member 24 when a single biasing member is provided) toward one another as biasing member is elastically deformed as contact members 12a,12b are rotated and squeezed together toward the reduced or closed configuration, sequentially shown in FIGS. 6D and 6E, respectively. Deformation and movement toward the reduced configuration may be performed manually, as in the case when a operator is preparing to insert the distal end portion of device 10 through a tube, obturator sleeve or other small opening, or by withdrawing device 10 from a surgical site, through a tube, obturator sleeve or other small opening, in which case the mechanical forces against vacuum line(s), mechanical closing rods and/or the contact members themselves act to reduce the configuration of contact members 12a,12b in the same manners as described above with regard to FIGS. 1-5. The example shown in FIG. 68 includes vacuum passages 28 in contact members 12a,12b that are designed to receive suction tubes 22. In this case, as suction tubes 22 are drawn through the small opening, the forces on suction tubes 22 act to rotate contact members 12a,12b in the manner described above, and as shown in FIG. 6D. Alternatively, a mechanical arrangement may be provided to assist in rotating contact members 12a,12b in the manner described, For example, an arrangement as described above with regard to the example of FIG. 5 may be provided to an arrangement as described with regard to FIGS. 6A-6E.

Contact members 12a, 12b are mounted to biasing member(s) 24 so that contact members 12a12b cannot rotate about their longitudinal axes with respect to biasing member 24. Thus, when contact members are forced to the intermediate configuration shown in FIG. 6D, the rotation of contact members 12a,12b also rotates or twists at least a portion of biasing member 24 thereby causing biasing member 24 to store potential energy as it is elastically deformed.

In addition to the rotation of contact members 12a, 12b about their longitudinal axis, the movement of contact members 12a,12b to the reduced or closed configuration in this example includes tilting of contact members 12a,12b to substantially align contact members 12a,12b with the longitudinal axis $L_1$ of device 10 as shown in FIG. 6E. In the example shown in FIG. 6E, the longitudinal axes $L_2$, $L_3$ are substantially parallel with the longitudinal axis $L_1$ of device 10. This secondary action elastically deforms biasing member(s) 24 by elastically bending the same about an axis $A_3$ that is normal to the axes of rotation $A_1$,$A_2$ about which biasing member(s) 24 was twisted during rotation of contact members 12a,12b as described above with regard to FIG. 6D. This bending deformation stores potential energy in biasing member 24 that is converted to kinetic energy to tilt the contact members 12a, 12b back to the tilt orientation shown in FIG. 6C when the external closing forces on the working end 12 have been released.

It should be further noted that the rotation and tilting actions do not necessarily proceed sequentially. For example, contact members 12a,12b may begin to be tilted before they are fully rotated to the closed position shown in FIG. 6D, as contact members 12a,12b may begin to abut against the small opening, tube or the like as they are being withdrawn, thereby initiating the tilting motion. As another example, an operator may choose to fully perform the tilting of contact members 12a,12b to the closed position prior to rotating the same to the closed position, effectively reversing the order of the movements shown in FIGS. 6D and 6E, prior to inserting the working end 12 through a small opening.

Stops 26 may be provided to define the end position of contact members 12a,12b in the open or operating configuration. Stops 26 may function as end points for both rotation and tilting so that biasing member 24 retains some potential energy to be applied about both the rotational and tilting axes ($A_1$,$A_2$,$A_3$), so that positive biasing forces are applied in both the tilting and rotational directions to maintain contact members 12a,12b against stops 26 during usage. Thus, for example, in the case where contact members 12a,12b apply suction to stabilize the tissue, when suction is applied and contact members 12a,12b are slightly raised or retracted to apply additional tension to the tissue grasped by contact members 12a,12b, the residual biasing forces applied by biasing member 24 ensure that contact members 12a,12b remain in the operational position against stops 26 and are not rotated or tilted in the directions toward the closed configuration.

In embodiments where arm 14 is permanently connected to the distal end portion of device 10, the interconnection between arm 14, base 16 and contact members 12a,12b may be arranged to combine the functions of locking the position/orientation of the contact members 12a,12b as well as arm 14 with the same mechanism. For example, as shown in the partial, sectional view of FIG. 7A, arm 14 may be provided as a series of ball joints 14b and links or sleeves 14s. Alternative configurations may include a series of ball joints each having a convex surface and a concave surface for example. Other examples of configurations for a flexible arm that may be locked with the use of a tensioning cable are described in application Ser. No. 10/615,007, filed Jul. 8, 2003 and titled "Organ Manipulator Apparatus", or in U.S. application Ser. No. 10/799,528, filed Mar. 13, 2004 and titled "Surgical Instruments for Stabilizing a Localized Portion of a Beating Heart", both of which are incorporated herein, in their entireties, by reference thereto, as well as in U.S. Pat. No. 6,758,808 which was incorporated by reference above.

Figure 7A:
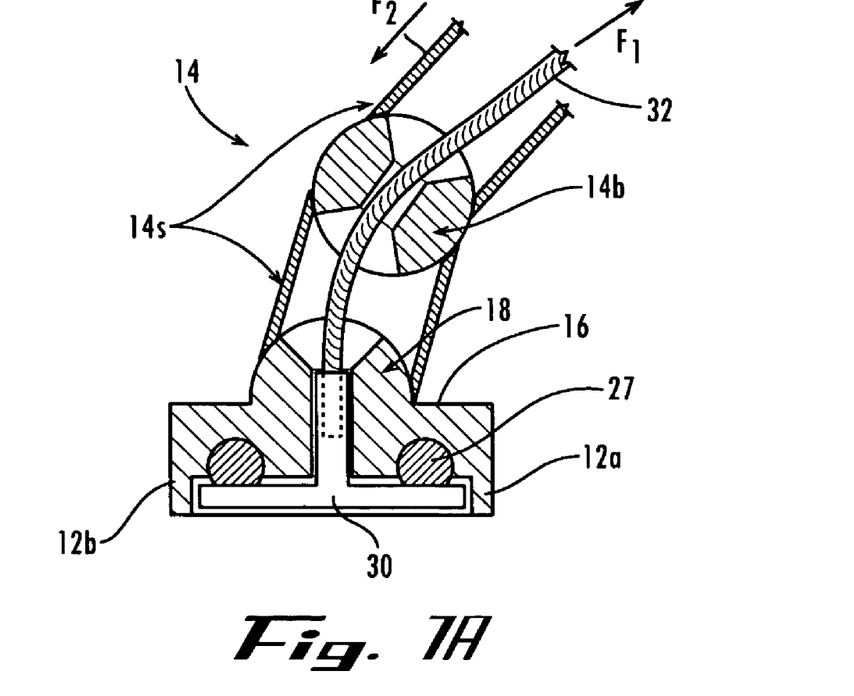
FIG. 7A is a sectional view illustrating a locking member used in locking both the arm and the contact members of a device.

The distal-most ball joint 18 may be fixed to or integral with base 16 as shown, or halves of such ball joint may be fixed to or integral with proximal ends of contact members 12a,12b. A locking member 30, such as a T-bar or disk with a stem extending perpendicular thereto, or the like is connected to a cable 32 or other flexible line resistant to deformation under tension, and cable 32 passes through the entirety of arm 14 to be connected with a tensioner at a proximal end portion of the device (not shown). Configurations for such a tensioner may be found by referring to U.S. Pat. No. 6,758,808, or U.S. application Ser. No. 10/799,528 which is incorporated herein, in its entirety, by reference thereto. After inserting the working end 12 of device 10 through a tube or other small opening and allowing contact members 12a,12b to assume the operational configuration, device 10 may be locked into a configuration determined by the operator to be useful for stabilizing tissue that is contacted by contact members 12a12b. Thus, the position/orientation of contact members 12a,12b is fixed with the same action that fixes the orientation/positioning of arm 14.

Figure 7B:
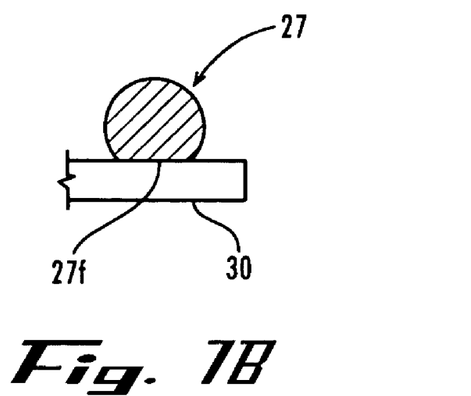
FIG. 7B is a partial sectional view showing an axle with a flat spot, wherein the flat spot is engaged by a locking member.
Figure 7C:
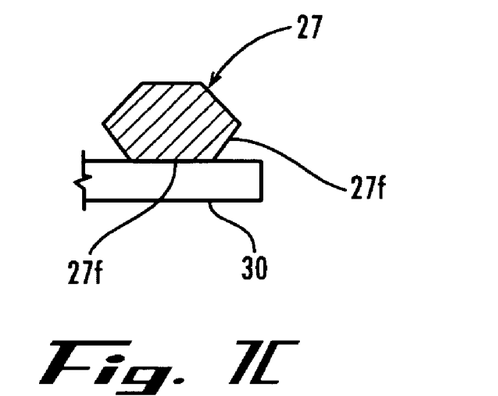
FIG. 7C is a partial sectional view showing an axle with multiple flat spots, wherein one of the flat spots is engaged by a locking member.

To lock device 10 into an operational configuration, tension is applied to cable 32 (in the direction of arrow $F_1$) which in turn forces sleeves 14s and balls 14b in the direction of arrows $F_2$, while providing an opposite force on locking member 30, which draws locking member 30 into contact with rods, shafts or axles 27 with sufficient force to prevent rotation of the rods, shafts or axles 27 with respect to base 16. Shafts rods or axles may be provided with one or more "flat spots" 27f (see FIGS. 7B and 7C) against which locking member may engage with compression force, for better resistance against rotation of contact members 12a,12b. Note that for this configuration, rods, shafts or axles 27 must be fixed with respect to contact members 12a,12b at all times so that when locking member 30 prevents rotation of rods, shafts or axles 27 with respect to base 16 as described, this also prevents any further rotation of contact members 12a,12b with respect to base and thus with respect to device 10. The locking mechanism thus locks contact members 12a,12b and draws ball joints 14b and sleeves 14s into compression against one another. Thus, by applying compression forces to rods, axles or shafts 27, base 16, and the sleeves 14s and balls 14b of arm 14, contact members 12a,12b are fixed in their configurations, and, at the same time, the remaining ball joints 14b and sleeves 14s are compressed against one another to lock the current configuration of arm 14 as well as to lock the orientation of arm 14 with respect to contact members 12a,12b.

Note that tension may be released or partially released from tensioning member 32 to allow slight repositioning of the components of device 10 and then tension may be re-established with sufficient force to lock all components for use in a different orientation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A device for stabilizing tissue within a patient's body, said device adapted to assume a reduced configuration and an operating configuration, said device assuming said reduced configuration for passage through a small opening to deliver a working end of said device to a site of the tissue to be stabilized, said device comprising:

a base member having a distal end portion and a proximal end portion;

first and second contact members extending distally and directly from said distal end portion of said base member and a joint member extending proximally from said proximal end portion of said base member, said contact members being mounted for rotation with respect to said base member; said contact members each having a contact surface adapted to contact a surface of the tissue, and said joint member being configured to mate with a mating joint member of a support arm to allow articulation of said base member relative to said support arm, and wherein locations of said distal end portion that said contact members extend from are not movable relative to each other as the device moves from a reduced configuration to an operating configuration:

wherein when said device is in said operating configuration, said contact surfaces face in a direction to contact the tissue, and when in said reduced configuration, said contact members have been rotated with respect to one another so that said contact surfaces substantially face one another; said first and second contact members extending along first and second longitudinal axes, respectively, wherein said first and second longitudinal axes of said first and second contact members remain parallel to one another when moving from said reduced configuration to said operating configuration;

wherein said first and second contact members rotate about said first and second longitudinal axes, respectively, and wherein said first and second contact members are further mounted for tilting with respect to said base member about an axis that is normal to said first and second longitudinal axes; wherein when in said reduced configuration, said contact members are substantially aligned with a longitudinal axis of said device, and wherein when in said operating configuration, said contact members are angled with respect to said longitudinal axis of said device; and wherein said contact members are biased about said axis that is normal to said first and second longitudinal axes toward said operating configuration.

2. The device of claim 1, further comprising stops extending from said base member, said stops are adapted to be contacted by said contact members when rotating from said reduced configuration to said operating configuration.

3. The device of claim 2, further comprising biasing members adapted to bias said contact members toward said operating configuration and against said stops.

4. The device of claim 1, further comprising biasing members adapted to bias said contact members toward said operating configuration.

5. The device of claim 4, wherein said biasing members comprise torsion springs interconnecting said first and second contact members with said base member, respectively.

6. The device of claim 1, wherein said first and second longitudinal axes form an acute angle with said longitudinal axis of said device when said contact members are in said operating configuration.

7. The device of claim 1, further comprising stops extending from said base member, said stops adapted to be contacted by said contact members when rotating and tilting from said reduced configuration to said operating configuration.

8. The device of claim 1, further comprising at least one biasing member adapted to bias said contact members toward said operating configuration, said at least one biasing member biasing each said contact member about said axis of said tilting and biasing each said contact member about said axis of said rotating.

9. The device of claim 1, further comprising said support arm and said mating joint member attached to said joint member of said base member, said support arm extending proximally from said base member.

10. The device of claim 9, wherein said arm is adapted to be locked to, and released from said base member.

11. The device of claim 9, wherein said arm is permanently connected to said base member.

12. The device of claim 9, wherein said arm is configured to assume an unlocked configuration and a locked configuration, wherein said arm is adjustable relative to said base member when in said unlocked configuration, and wherein said arm is fixed relative to said base member when in said locked configuration.

13. The device of claim 9, further comprising a locking member adapted to interact with locking of said arm, wherein upon locking said arm in said locked configuration, said contact members are also locked in said operating configuration.

14. The device of claim 9, wherein said first and second contact members are configured to be automatically driven to said reduced configuration when said device is drawn through an opening having a cross-section smaller than a cross-section of said contact members in said operating configuration.

15. The device of claim 14, wherein said first and second contact members are configured to apply suction to a surface of the tissue, said device further comprising first and second suction lines extending from said first and second contact members respectively, said first and second suction lines extending proximally of said base member and configured to facilitate the driving to said reduced configuration as said first and second suction lines are drawn through said opening.

16. The device of claim 15, wherein said first and second suction lines follow external contours of said arm.

17. The device of claim 15, wherein said first and second suction lines pass within said arm.

18. The device of claim 14, further comprising first and second substantially rigid members extending from said first and second contact members respectively, said first and second substantially rigid members extending proximally of said base member and configured to facilitate the driving to said reduced configuration as said first and second substantially rigid members are drawn through said opening.

19. The device of claim 18, further comprising a first ring slidably positioned over said arm and connected directly to said first substantially rigid member; and a second ring slidably positioned over said arm and connected directly to said second substantially rigid member.

20. The device of claim 14, wherein proximal portions of said first and second contact members are tapered to facilitate automatic driving of said first and second contact members to said reduced configuration as said tapered portions are drawn into the opening.

21. The device of claim 1, wherein, when in said operating configuration, the largest cross-sectional dimension of the working end of said device is greater than any cross-sectional dimension of the small opening.

22. The device of claim 1, wherein said first and second contact members are configured to be automatically driven to said reduced configuration when said device is drawn through an opening having a cross-section smaller than a cross-section of said contact members in said operating configuration.

23. The device of claim 22, wherein said first and second contact members are configured to apply suction to a surface of the tissue, said device further comprising first and second suction lines extending from said first and second contact members respectively, said first and second suction lines extending proximally of said base member and configured to facilitate the driving to said reduced configuration as said first and second suction lines are drawn through said opening.

24. The device of claim 22, further comprising first and second rigid members extending proximally from said first and second contact members respectively, said first and second rigid members also extending proximally of said base member, said first and second rigid members facilitating the driving to said reduced configuration as said first and second rigid members are drawn through said opening.

25. The device of claim 22, wherein proximal portions of said first and second contact members are tapered to facilitate automatic driving of said first and second contact members to said reduced configuration as said tapered portions are drawn into the opening.

26. The device of claim 22, further comprising first and second rods, bars or wires extending proximally from said first and second contact members respectively, said first and second rods, bars or wires also extending proximally of said base member, said first and second rods, bars or wires facilitating the driving to said reduced configuration as said first and second rods, bars or wires are drawn through said opening.

27. A device for stabilizing tissue within a patient's body, said device adapted to assume a reduced configuration for passage through a small opening to deliver a working end of said device to a site of the tissue to be stabilized, said device comprising:
first and second contact members extending directly from a base member, said contact members being mounted for rotation with respect to said base member, said contact members each having a contact surface adapted to contact a surface of the tissue, said contact members configured to assume a reduced configuration and an operating configuration, wherein when said contact members are in said operating configuration, said contact surfaces face in a direction to contact the tissue, and when in said reduced configuration, said contact members have been rotated with respect to one another so that said contact surfaces substantially face one another;
an arm extending proximally from said base member;
a structure extending from said contact members proximally past said base member and configured to facilitate automatic movement of said contact members from said operating configuration to said reduced configuration as said structure is drawn through said opening, without movement of said base member; and
at least one biasing member configured to drive movement of said contact members from said reduced configuration to said operating configuration.

28. The device of claim 27, wherein said arm is configured to assume an unlocked configuration and a locked configuration, wherein said arm is adjustable relative to said contact members when in said unlocked configuration, and wherein said arm is fixed relative to said contact members member when in said locked configuration, said device further comprising a locking member and a tensioning member, wherein application of tension to said tensioning member draws said locking member, locking said arm and contact members.

29. The device of claim 28, wherein said tensioning member passes through said arm.

30. The device of claim 28, wherein said arm is flexible in said unlocked configuration and rigid in said locked configuration.

31. The device of claim 27, wherein said first and second contact members are further mounted for tilting with respect to said arm; wherein when in said reduced configuration, said contact members are substantially aligned with a longitudinal axis of said device, and wherein when in said operating configuration, said contact members are angled with respect to said longitudinal axis; and wherein said at least one biasing member is configured to additionally drive automatic tilting of said contact members.

32. The device of claim 27, wherein said at least one biasing member continuously biases said contact member toward said operating configuration, when said contact members are in said reduced configuration, and when said contact members are moved from said operating configuration to said reduced configuration.

33. A device for stabilizing tissue within a patient's body, said device including first and second contact members that assume a reduced configuration for passage through a small opening for deliverance to a site of the tissue to be stabilized, said device comprising:
a base member;
said first and second contact members extending distally and directly from said base member, said contact members being mounted for rotation with respect to said base member; said contact members each having a contact surface adapted to contact a surface of the tissue, and wherein portions of said base member, at locations where said contact members extend from, are not movable relative to each other as the device moves from a reduced configuration to an operating configuration;
wherein when said contact members are in an operating configuration, said contact surfaces face in a direction to contact the tissue, and when in said reduced configuration, said contact members have been rotated with respect to one another so that said contact surfaces substantially face one another; said first and second contact members extending along first and second longitudinal axes, respectively;

wherein said first and second contact members rotate about said first and second longitudinal axes, respectively, and a joint interconnecting said base member with an elongated support arm;

wherein said joint is operable between an unlocked configuration to allow articulation of said base member relative to said support arm and a locked configuration to prevent articulation of said base member relative to said support arm, and wherein said joint is operable independently of operation of said contact members relative to said base member.

* * * * *

UNITED STATES PATENT AND TRADEMARK OFFICE
CERTIFICATE OF CORRECTION

| | | |
|---|---|---|
| PATENT NO. | : 8,083,664 B2 | Page 1 of 1 |
| APPLICATION NO. | : 11/137267 | |
| DATED | : December 27, 2011 | |
| INVENTOR(S) | : Davis | |

It is certified that error appears in the above-identified patent and that said Letters Patent is hereby corrected as shown below:

Column 9, line 13, please delete "FIG. 68" and insert -- FIG 6B --.

Signed and Sealed this
Twenty-third Day of October, 2012

David J. Kappos
*Director of the United States Patent and Trademark Office*